(12) United States Patent
Hynna et al.

(10) Patent No.: US 10,376,250 B2
(45) Date of Patent: Aug. 13, 2019

(54) AUTOMATED AUTOPSY SYSTEM

(71) Applicants: Kai Michael Hynna, Toronto (CA);
Joshua Lee Richmond, Toronto (CA);
Alexander Gyles Panther, Toronto
(CA); Thanh Vinh Vuong, Toronto
(CA)

(72) Inventors: Kai Michael Hynna, Toronto (CA);
Joshua Lee Richmond, Toronto (CA);
Alexander Gyles Panther, Toronto
(CA); Thanh Vinh Vuong, Toronto
(CA)

(73) Assignee: **SYNAPTIVE MEDICAL
(BARBADOS) INC.**, Bridgetown (BB)

( * ) Notice: Subject to any disclaimer, the term of this patent is extended or adjusted under 35 U.S.C. 154(b) by 205 days.

(21) Appl. No.: 14/902,723

(22) PCT Filed: Mar. 23, 2015

(86) PCT No.: PCT/CA2015/050223
§ 371 (c)(1),
(2) Date: Jan. 4, 2016

(87) PCT Pub. No.: WO2016/149788
PCT Pub. Date: Sep. 29, 2016

(65) Prior Publication Data
US 2018/0000467 A1    Jan. 4, 2018

(51) Int. Cl.
*A61B 16/00*       (2006.01)
*A61B 34/20*       (2016.01)
(Continued)

(52) U.S. Cl.
CPC .............. *A61B 16/00* (2013.01); *A61B 34/20*
(2016.02); *A61B 90/36* (2016.02); *G16H 40/63* (2018.01);
(Continued)

(58) Field of Classification Search
USPC .......................................................... 606/1
See application file for complete search history.

(56) References Cited

U.S. PATENT DOCUMENTS

| 8,079,950 B2 | 12/2011 | Stern et al. | |
| 2004/0014165 A1* | 1/2004 | Keidar | G06F 19/321 |
| | | | 435/40.5 |

(Continued)

FOREIGN PATENT DOCUMENTS

WO    WO201348957    4/2013

OTHER PUBLICATIONS

Soltanzadeh et al., "Application of robotic assisted technology and imaging devices in autopsy and virtual autopsy", IJCSI Internationa, IJCSI International Journal of Computer Science Issues, vol. II, Issue 4, No. 2, pp. 104-109, Jul. 2014.

(Continued)

*Primary Examiner* — Aaron F Roane
(74) *Attorney, Agent, or Firm* — Ridout & Maybee LLP

(57) ABSTRACT

A medical navigation system is provided for performing at least part of an assessment of a non-living body. The medical navigation system comprises a positioning device having a positioning arm with an end effector at the end of the positioning arm, an imaging device coupled to the end effector, and a controller electrically coupled to the positioning device and the imaging device. The controller has a processor coupled to a memory and a display. The controller is configured to generate a signal to move the positioning arm to position the imaging device through a range of motion to perform a scan of a surface of the body and receive and save as data in the memory signals generated by the imaging device during the range of motion.

8 Claims, 6 Drawing Sheets

(51) Int. Cl.
*A61B 90/00* (2016.01)
*G16H 40/63* (2018.01)

(52) U.S. Cl.
CPC ..... *A61B 90/361* (2016.02); *A61B 2034/2055* (2016.02); *A61B 2090/374* (2016.02); *A61B 2090/376* (2016.02); *A61B 2090/378* (2016.02); *A61B 2090/3735* (2016.02)

(56) References Cited

U.S. PATENT DOCUMENTS

2004/0015053 A1* 1/2004 Bieger ............... A61B 1/00149
 600/117
2005/0267359 A1 12/2005 Hussaini et al.

OTHER PUBLICATIONS

Peled, Roee, "Mantis Vision Field Applications: Infrared Laser Scanning for Multi-Disciplinary Field Applications", Microsoft Power Point presentation, Jul. 2013 p. 1 to 16.
Schweitzer et al, "Photography, X-rays, Computed Tomography" Imaging Insights vol. 14, Issue 2, Virtopsy.

* cited by examiner

AUTOMATED AUTOPSY SYSTEM

TECHNICAL FIELD

The present disclosure is generally related to automated medical equipment, and more specifically to an automated autopsy system.

BACKGROUND

The present disclosure is generally related to image guided medical procedures using a surgical or diagnostic instrument, such as an optical scope, an optical coherence tomography (OCT) probe, a micro ultrasound transducer, an electronic sensor or stimulator, a camera or 3D camera or scanner, magnetic resonance (MR) imaging transducers, x-ray systems, or computed tomography (CT) scanners.

Autopsies are very slow processes for pathologists, as they have to perform a comprehensive visual scan as well as internal dissection of various parts of the cadaver. Some cultures want the deceased's body returned as soon as possible or object to any type of internal tests on the body.

Conventional autopsy systems have not offered any solutions to these problems. It would be desirable to have an autopsy system that aims to accelerate autopsies, create better data for later use after an autopsy is performed, and provides less invasive options for medical professionals wishing to perform an autopsy.

SUMMARY

One aspect of the present disclosure provides a medical navigation system for performing at least part of an autopsy of a non-living body. The medical navigation system comprises a positioning device having a positioning arm with an end effector at the end of the positioning arm, an imaging device coupled to the end effector, and a controller electrically coupled to the positioning device and the imaging device. The controller has a processor coupled to a memory and a display. The controller is configured to generate a signal to move the positioning arm to position the imaging device through a range of motion to perform a scan of a surface of the body and receive and save as data in the memory the signals generated by the imaging device during the range of motion.

Another aspect of the present disclosure provides a method for performing at least part of an automated autopsy of a body using a medical navigation system having a positioning device having a positioning arm with an imaging device coupled to the positioning arm and a controller electrically coupled to the positioning device and the imaging device. The controller has a processor coupled to a memory and a display. The method comprises generating a signal to move the positioning arm to position the imaging device through a range of motion to perform a scan of a surface of the body and receiving and saving as data in the memory the signals generated by the imaging device during the range of motion.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Figure 1:
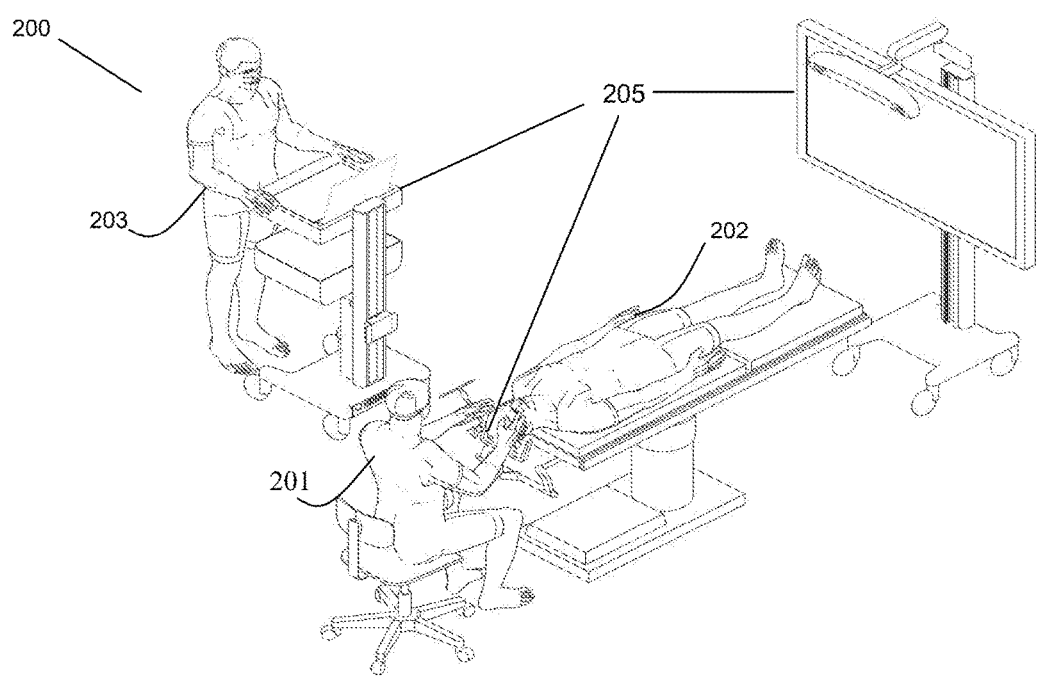
FIG. 1 shows an exemplary navigation system to support minimally invasive surgery that may also be applied to performing an automated autopsy.

Referring to FIG. 1, an exemplary navigation system environment 200 is shown, which may be used to support navigated image-guided surgery. As shown in FIG. 1, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 2:
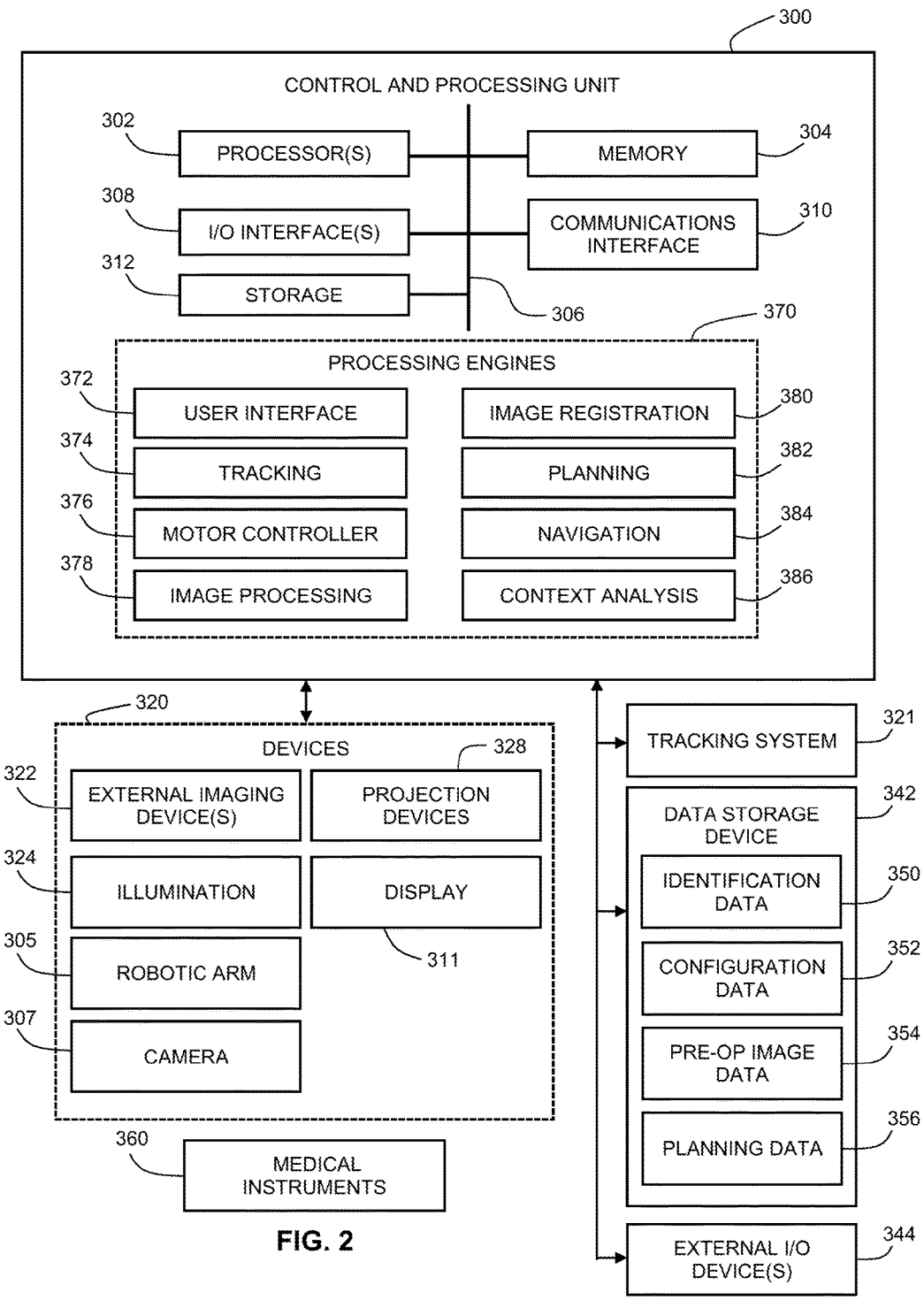
FIG. 2 is a block diagram illustrating a control and processing system that may be used in the navigation system shown in FIG. 1.

Referring to FIG. 2, a block diagram is shown illustrating a control and processing system 300 that may be used in the medical navigation system 200 shown in FIG. 1 (e.g., as part of the equipment tower). As shown in FIG. 2, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 2, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 2, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 2, include one or more external imaging devices 322, one or more illumination devices 324, a robotic arm 305, one or more projection devices 328, and one or more displays 205, 311.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 2, in one example the processing modules 370 may be stored in the memory 304 and the processing modules may be collectively referred to as processing modules 370.

It is to be understood that the system is not intended to be limited to the components shown in FIG. 2. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools perform an automated autopsy. In addition to performing automated autopsies, the navigation system 205 may also be applied to the removal of brain tumours and intracranial hemorrhages (ICH). The navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 3:
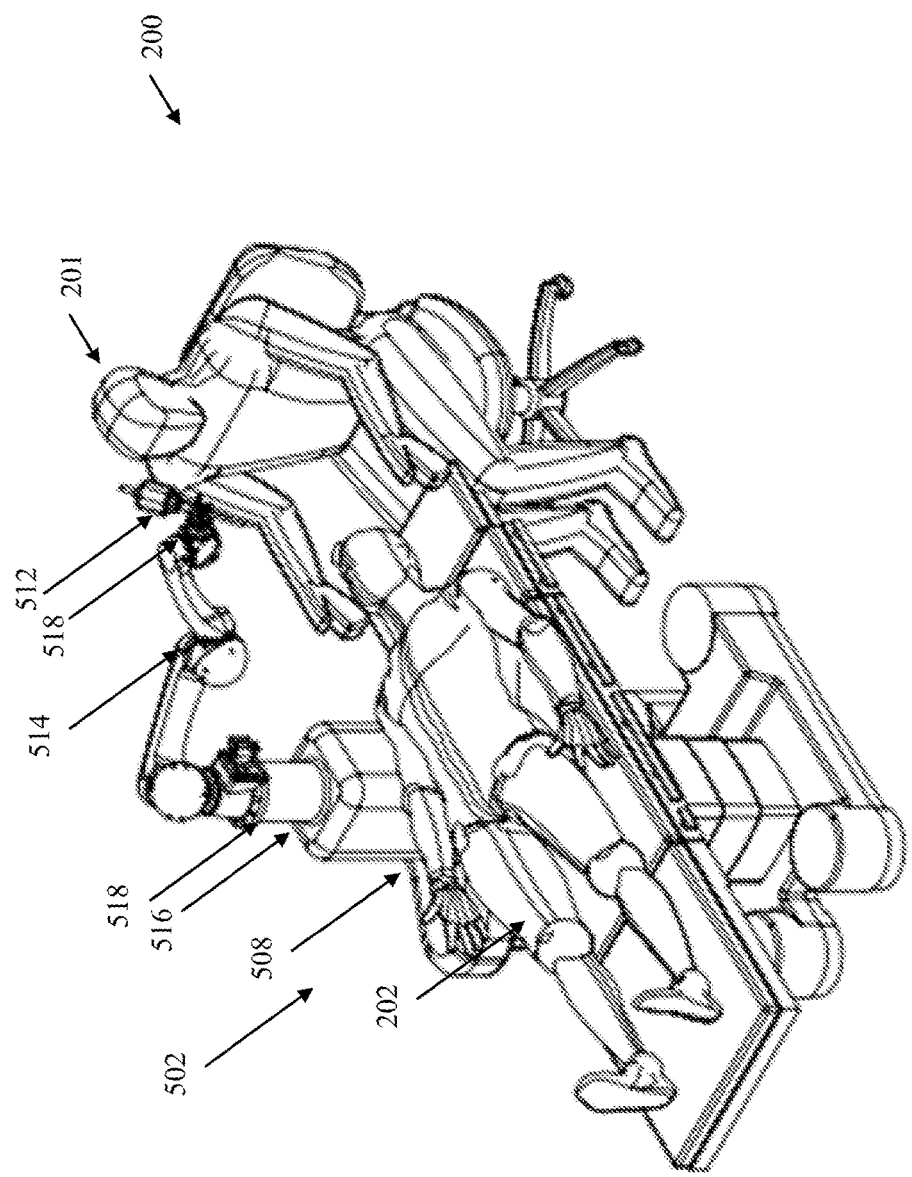
FIG. 3 is an exemplary navigation system similar to FIG. 1 illustrating system components of an exemplary surgical system that may be used in performing an automated autopsy.

FIG. 3 is a diagram illustrating components of an exemplary surgical system that may used in an automated autopsy system that is similar to FIG. 1. FIG. 3 illustrates a navigation system 200 having an equipment tower 502, a tracking system and a display (not shown), an intelligent positioning system 508 and optional tracking markers (not shown) that may be used to track instruments. In the example of an automated autopsy, the surgeon 201 may not be present and the navigation system 200 may function in a fully automated or partially automated mode. The imaging device 512 may be an external scope, videoscope, wide field camera, or an alternate image capturing device such as a 3D camera. The imaging sensor view is depicted on the visual display which surgeon 201 may use for navigating through the anatomical region of interest. The system of FIG. 3 may also be applied to an automated autopsy system, described in more detail below.

An intelligent positioning system 508 comprising an automated arm 514, a lifting column 516 and an end effector 518, is placed in proximity to patient 202. Lifting column 516 is connected to a frame of intelligent positioning system 508. In another example, the intelligent positioning system 508 may be fixed to a table or horizontal surface and the patient 202 may be placed in an autopsy area. As seen in FIG. 3, the proximal end of automated mechanical arm 514 (further known as automated arm herein) is connected to lifting column 516. In other embodiments, automated arm 514 may be connected to a horizontal beam, which is then either connected to lifting column 516 or directly to frame of the intelligent positioning system 508. Automated arm 514 may have multiple joints to enable 5, 6 or 7 degrees of freedom.

End effector 518 is attached to the distal end of automated arm 514. End effector 518 may accommodate a plurality of instruments or tools that may assist surgeon 201 in his procedure or provide a number of functions in the case of an automated autopsy. In the example of an automated autopsy system, there may be a coroner or technician 201 supervising the automated autopsy, which is entirely or at least partially automatically performed by the navigation system 200. End effector 518 is shown as holding an external scope, however it should be noted that this is merely an example and alternate devices may be used with the end effector 518 such as a wide field camera, microscope and OCT (Optical Coherence Tomography), such as an optical scope, a micro ultrasound transducer, an electronic sensor or stimulator, a camera or 3D camera or scanner, a magnetic resonance (MR) imaging transducers, an x-ray systems, or computed tomography (CT) scanner, or other imaging instruments. In another example, multiple end effectors may be attached to the distal end of automated arm 518, and thus assist the surgeon 201 in switching between multiple modalities. For example, the coroner or technician 201 may want the ability to move between microscope and OCT with stand-off optics. In a further example, the ability to attach a second, more accurate, but smaller range end effector such as a laser based ablation system with micro-control may be contemplated.

The intelligent positioning system 508 receives as input the spatial position and pose data of the automated arm 514 and target as determined by the tracking system, in one example by detection of tracking markers on the patient 202 by the wide field camera. Further, it should be noted that the tracking markers may be used to track both the automated arm 514 as well as the end effector 518 either collectively or independently. It should be noted that a wide field camera 520 is shown in this image and that it is connected to the external scope (e.g., imaging device 512) and the two imaging devices together are held by the end effector 518. It should additionally be noted that although these are depicted together for illustration of the diagram that either could be utilized independently of the other, for example where an external video scope can be used independently of the wide field camera 520.

Intelligent positioning system 508 computes the desired joint positions for automated arm 514 so as to maneuver the end effector 518 mounted on the automated arm's distal end to a predetermined spatial position and pose. This redetermined relative spatial position and pose is termed the "Zero Position" where the sensor of imaging device 512 and the desired viewing axis are axially aligned.

Further, the intelligent positioning system 508, optical tracking device, automated arm 514, and tracking markers may form a feedback loop. This feedback loop works to keep the desired view in constant view and focus of the end effector 518. Intelligent positioning system 508 may also include a foot pedal (or other input devices, such as touch sensors, motion sensors, microphone, mechanical buttons, etc.) for use by the surgeon 201 to align the end effector 518 (i.e., holding a videoscope) of automated arm 514 with the desired viewing target.

Figure 4:
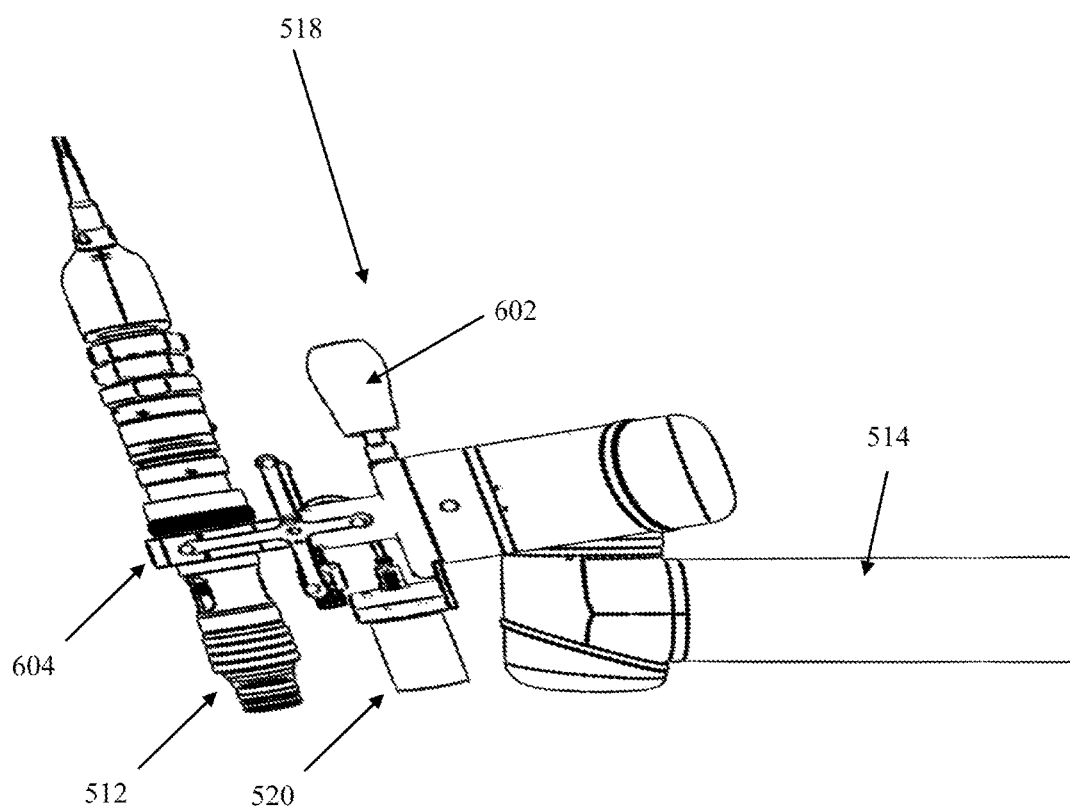
FIG. 4 is perspective drawing illustrating an end effector holding a camera.

Referring to FIG. 4, an end effector 518 is shown attached to automated arm 514. The end effector 518 includes a handle 602 and a scope clamp 604. The scope clamp 604 holds imaging device 512. The end effector also has wide field camera 520 attached thereto. An end effector similar to the end effector 518 may be used for and/or adapted to holding any of the imaging devices, probes, needles, or other medical equipment described below for use in performing an automated autopsy.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The present application may be applied to a navigation system such as the navigation system 200 for the purpose of performing and/or aiding in an autopsy. Given a cadaver, a doctor must perform a visual inspection of the surface of the skin for any areas of interest. A suitably programmed navigation system may initiate and perform a complete and thorough body scan, possibly at multiple angles, identifying and/or cataloging any issues that are found. If an item of interest on the skin is automatically discovered by the navigation system (e.g., bruising, cuts, etc.), then the navigation system 200 may automatically generate additional images in the area of the item of interest. In one example, the additional images may be of a particularly high resolution. Such an approach may have a number of benefits, such as: (a) the pathologist now has a digital record of the body that he can go back and look at if other questions arise later on; (b) a suitable camera may be used in order to pick up wavelengths of light not observable by human eyes; and/or (c) the doctor may perform the automated initial scan on the body and use that as a guide to speed up his autopsy procedure. For example, if the navigation system finds no unusual problems on the skin of the body then the doctor may skip that step and move to internal steps of the autopsy.

In some examples, the present application may also aim to: (a) automatically take tissue samples of different organs (e.g., after a special registration of the body, determine where the liver is and insert a biopsy probe to extract a sample of the liver); (b) provide additional scanning modalities, such as ultrasound, x-ray, computed tomography (CT), positron emission tomography (PET), magnetic resonance imaging (MRI), etc.; (c) provide a 3D scanner that may provide full body surface 3D information; (d) perform a full body MRI; (e) provide for a tele-operated or remotely controlled autopsy using a the navigation system, such as in the case of body that may present a biomedical hazard; (f) provide insertable optical probes for performing automated biopsies; (g) provide a rapid toxicology analysis where tissue removal is not needed; (h) automatically determine a cause of death; and/or (i) provide for a MR guided automated biopsy using a long table or conveyer belt.

One aspect of the present application provides a medical navigation system, such as the medical navigation system 200, for performing at least part of an autopsy of a body (e.g., the patient or body 202). The medical navigation system 200 may include a positioning device, such as positioning system 508, having a positioning arm, such as automated arm 514, with an end effector, such as the end effector 518, at the end of the positioning arm. An imaging device 512 may be coupled to the end effector 518. A controller (e.g., control and processing unit 300) is electrically coupled to the positioning device and the imaging device. The controller has a processor (e.g., processor 302) coupled to a memory (e.g., memory 304 and/or data storage device 342) and a display (e.g., display 311 and/or 506). The controller is configured to generate a signal to move the positioning arm to position the imaging device 512 through a range of motion to perform a scan of a surface of the body 202 and receive and save as data in the memory 304/342 the signals generated by the imaging device 512 during the range of motion. The medical navigation system 200 may further have a horizontal surface for supporting the body, as shown in FIG. 3. In one example, the horizontal surface may be substantially transparent allowing the imaging device 512 to acquire images of a backside of the body as the imaging device is moved around the backside of the body underneath the horizontal surface by the positioning arm.

In one example, the imaging device 512 may be an optical camera such as a three dimensional (3D) camera. However, the imaging device 512 may be any suitable imaging device such as a video camera, a thermal camera, an acoustic receiver, a sonar device, an optical coherence tomography (OCT) device, or a polarization sensitive OCT (PS-OCT) device. In some examples, the imaging device 512 may include two or more such imaging devices used simultaneously or consecutively or the imaging devices may be changed during the automated autopsy, where one such imaging device is removed from the end effector 518 such that another imaging device may be attached to the end effector 518.

In one example, the medical navigation system 200 may be configured to perform a pathological analysis of the saved data to automatically discover items of interest on the surface of the body 202 and to further provide an initial assessment of a likely cause of death of the body 202. The pathological analysis may either be semi-automated or fully-automated by the medical navigation system 200. The saved data may be compared to data stored in a database as a basis for the pathological analysis. The saved data may also be stored in a repository as historical data for use in future autopsies.

In one example, in response to discovering an item of interest on the surface of the body 202, the medical navigation system 200 may be configured to generate a signal to move the positioning arm to position the imaging device 512 to capture additional images in an area of the item of interest on the surface of the body 202 and receive and save as additional data in the memory 304,342 the signals generated by the imaging device 512 during the capture of the additional images. In one example, a suitable imaging device may be used such that the imaging device 512 can detect wavelengths of light outside of the visible range therefore providing information for an automated analysis by the medical navigation system 200 beyond that which is directly observable by the human eye. For example, an imaging device capable of detecting infrared light may provide additional information about the surface of the body 202.

In one example, the medical navigation system 200 may have an ultrasound component that is connectable to the end effector 518 and electrically connectable to the controller. In one example, the ultrasound component may include an ultrasound transducer capable of generating ultrasonic waves for transmission through human tissue and capable of detecting reflections reflected by the tissue. The controller may be configured to generate a signal to move the positioning arm to position the ultrasound component through a range of motion to perform an automated ultrasound of an area of interest on the surface of the body 202 and receive and save as data in the memory 304,342 the signals generated by the ultrasound component during the range of motion.

In another example, the medical navigation system 200 may have an x-ray component that is connectable to the end effector 518 and electrically connectable to the controller. In one example, the x-ray component may include an x-ray transducer capable of generating x-rays for transmission through human tissue. The x-ray component may also include a second x-ray transducer that may be positioned on the other side of the body 202 that is capable of receiving x-rays that pass through the tissue of the body 202. The controller may be configured to generate a signal to move the positioning arm to position the x-ray component through a range of motion to perform an automated x-ray of an area of interest on the surface of the body and receive and save as data in the memory 304,342 the signals generated by the x-ray component that received the x-rays passed through the body 202 during the range of motion. In one example, the medical navigation system 200 may be configured to perform a whole body x-ray, since radiation exposure is no longer a concern for a body that is no longer living.

In another example, the medical navigation system 200 may have a magnetic resonance (MR) imaging component that is electrically connected to the controller. When the body is placed in the MR imaging component the controller is configured to generate a signal to operate the MR imaging component and receive and save as data in the memory 304,342 the signals generated by the MR imaging component during the operation of the MR imaging component.

In another example, the medical navigation system 200 may have a computed tomography (CT) imaging component that is electrically connected to the controller. When the body is placed in the CT imaging component the controller is configured to generate a signal to operate the CT imaging component and receive and save as data in the memory 304, 342 the signals generated by the CT imaging component during the operation of the CT imaging component.

Figure 5:
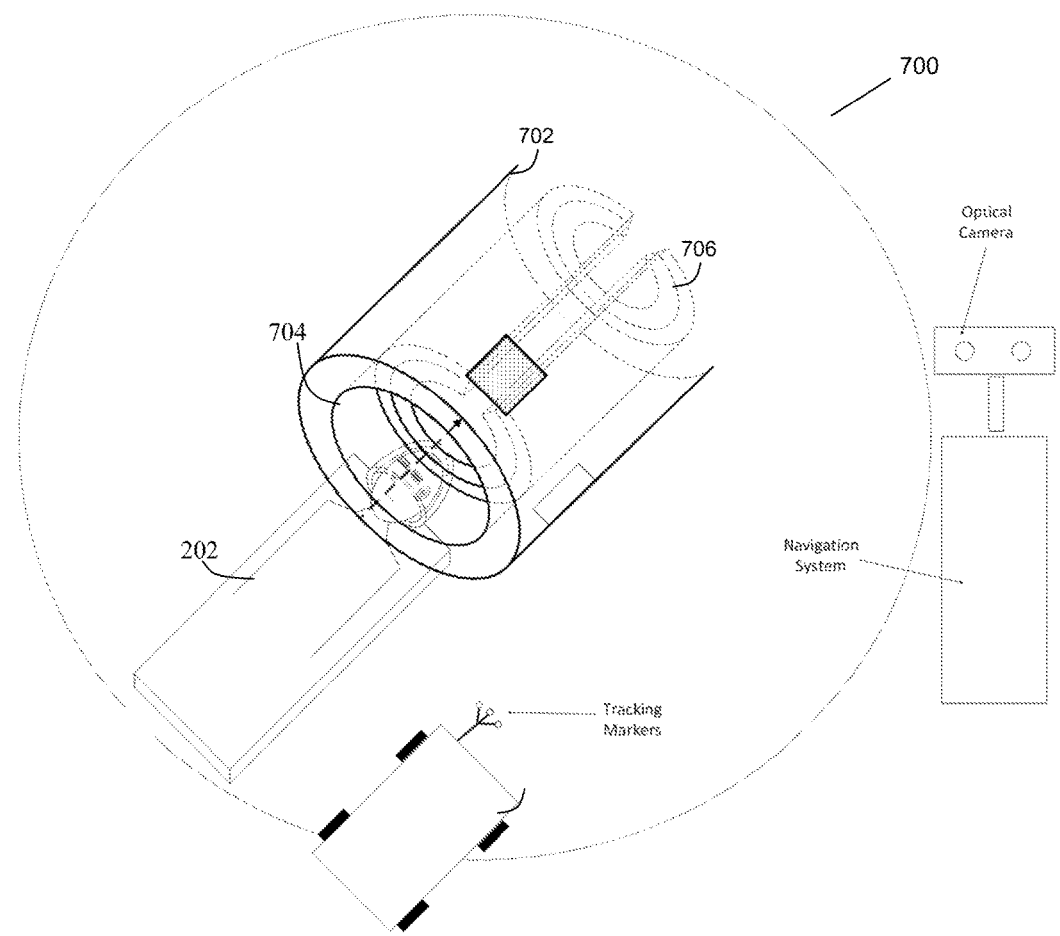
FIG. 5 is a perspective drawing illustrating a scanning module that may be used with the navigation system of FIG. 3.

Referring now to FIG. 5, a perspective drawing is shown illustrating an exemplary scanning module 700 that may be used with the medical navigation system 200. The scanning module 700 may include an enclosure 702 having an opening 704 to allow for entry of the body 202. In one example, the enclosure 702 may be cylindrical; however the enclosure 702 may be any suitable shape to meet the design criteria of a particular application. The scanning module 700 may include a coil 706 or series of coils 706 or other suitable transducer(s) for generating, transmitting, and/or receiving electromagnetic magnetic signals where the scanning module 700 is using for magnetic resonance imaging. In another example, the scanning module may be suitable for x-rays or CT scans. As such, the exemplary scanning module 700 may be used as the x-ray component, the MR imaging component, and/or the CT imaging component, or as any other suitable component. The horizontal surface of FIG. 3 may be moved into the scanning module 700 when the scanning module 700 is to be used or the scanning module 700 may be moved into position with the horizontal surface being fixed, depending on the design criteria of a particular application.

In one example, the medical navigation system 200 may have a biopsy probe that is connectable to the end effector 518. The controller may be configured to generate a signal to move the positioning arm to position the biopsy probe in a position to perform an automated biopsy of an area of interest in the body 202. The positioning arm may further retrieve and store a biopsy sample taken by the biopsy probe. In another example, the medical navigation system 200 may have a needle that is connectable to the end effector 518. The controller may be configured to generate a signal to move the positioning arm to position the needle in a position to take a blood sample from the body 202 and retrieve and store the blood sample taken by the needle.

In one example, the medical navigation system 200 may be remotely operated by an operator for performing at least a partially automated autopsy of a body that presents a biomedical hazard, such as a body that was infected with a virus that is highly contagious and deadly. The medical navigation system 200 may be controllable by an operator in another room observing through a window, or even remotely controllable by an operator who is offsite and observes the procedure remotely on a display, for example by video provided by a video camera connected to the medical navigation system 200.

In one example, the medical navigation system 200 may have a guided path electrically coupled to the controller. The MR imaging component and/or the CT imaging component and/or the xray component may be in the form of an enclosure (e.g., the scanning module 700 shown in FIG. 7) enclosing at least a portion of the guided path. In one example, the scanning module 700 is located a distance from the positioning device, the guided path or a horizontal surface that is moveable on the guided path that supports the body, and the controller controls the guided path and/or the horizontal surface on the guided path to automatically position the body for access by the positioning device, the CT imaging component, the MR imaging component, and/or the x-ray imaging component when needed. In one example, the guided path may be a conveyor belt, tracks, optical markers that may be followed by the positioning arm, or any other suitable solution that allows the medical navigation system 200 to move the body 202 for access by various components of an automated autopsy system.

Figure 6:
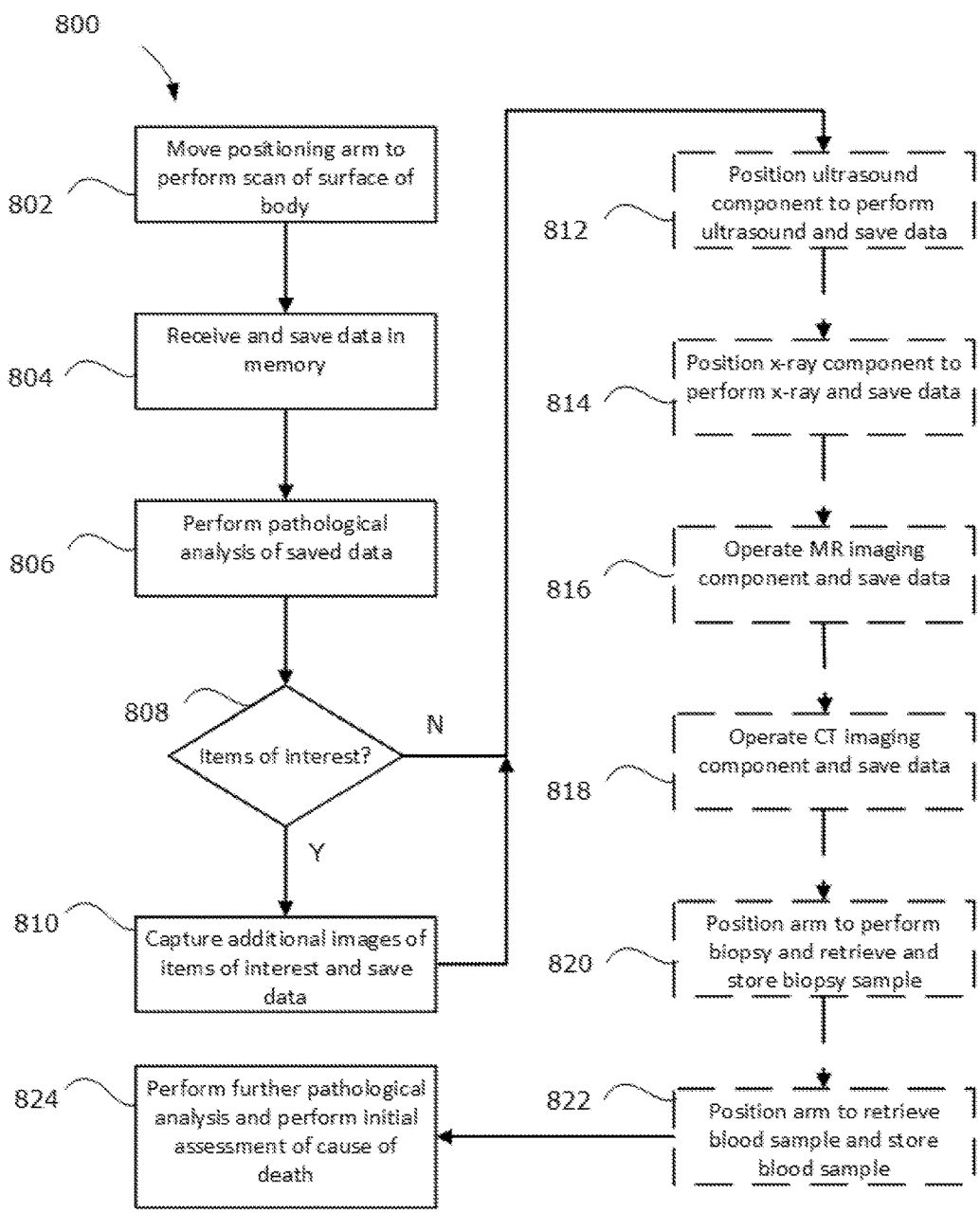
FIG. 6 is a flow diagram illustrating a method of performing an automated autopsy.

Referring now to FIG. 6, a flow diagram is shown illustrating a method 800 of performing an automated autopsy. The method 800 may be a method for performing at least part of an automated autopsy of a body (e.g., the body 202) using a medical navigation system (e.g., the medical navigation system 200) having a positioning device having a positioning arm (e.g., the automated arm 514) with an imaging device coupled to the positioning arm. A controller, such as the control and processing unit 300, is electrically coupled to the positioning device and the imaging device. The controller has a processor (e.g., the processor 302) coupled to a memory (e.g., the memory 304 and/or the data storage device 342) and a display (e.g., the display 311, 506). At a first block 802, the method 800 generates a signal to move the positioning arm to position the imaging device through a range of motion to perform a scan of a surface of the body and, at a block 804, receives and saves as data in the memory 304, 342 the signals generated by the imaging device during the range of motion.

In one example, the imaging device may be an optical camera, a three dimensional (3D) camera, a video camera, a thermal camera, an acoustic receiver, a sonar device, an optical coherence tomography (OCT) device, a polarization sensitive OCT (PS-OCT) device, any combination thereof, or any other suitable imaging device. The imaging device may be able to detect wavelengths of light outside of the visible range therefore providing information for an automated analysis beyond what is observable by the human eye.

Next, at a block 806, a pathological analysis of the saved data may be performed to automatically discover items of interest on the surface of the body 202. The pathological analysis may be semi-automated or fully-automated by the medical navigation system 200, depending on the design criteria of a particular application or the desire of a supervising technician or physician. In another example, the pathological analysis performed at the block 806 may be done during the scans (e.g., in parallel with the blocks 802/804) so that the imaging device scans a section of the body, the data is analyzed in parallel and the signal to capture more high-resolution images or scans by the imaging device (e.g., block 810 described below) may be generated before finishing blocks 802/804. In another example, the patient or cadaver 202 may be divided into regions, such as first performing a head scan (block 802/804), followed by a pathological analysis (block 806), along with any additional scans in any area of interest (block 810), at which point a next area of the body is focused on (e.g., blocks 802-810 are performed for the torso).

When one or more items of interest are found on the surface of the body 202, the method 800 proceeds to a block 810 where a signal is generated to move the positioning arm to position the camera to capture additional images in an area of the item of interest on the surface of the body 202 and receive and save as additional data in the memory 304, 342 the signals generated by the imaging device during the capture of the additional images.

After the blocks 806 and 810, if applicable, an initial assessment of a likely cause of death may be provided at a block 824. A number of optional blocks 812, 814, 816, 818, 820, and 822 may be performed, indicated by broken lines, depending on the design criteria of a particular application and/or the judgment of a supervising technician or physician.

At an optional block 812, the system may have an ultrasound component that is connectable to the positioning arm and electrically connected to the controller. The method 800 may generate a signal to move the positioning arm to position the ultrasound component through a range of motion to perform an automated ultrasound of an area of interest on the surface of the body 202 and receive and save as data in the memory 304,342 the signals generated by the ultrasound component during the range of motion.

At an optional block 814, the system may have an x-ray component that is connectable to the positioning arm and electrically connectable to the controller. The method 800 may generate a signal to move the positioning arm to position the x-ray component through a range of motion to perform an automated x-ray of an area of interest on the surface of the body 202 and receive and save as data in the memory 304,342 the signals generated by the x-ray component during the range of motion.

At an optional block 816, the system may have a magnetic resonance (MR) imaging component that is electrically connected to the controller. When the body 202 is placed in the MR imaging component, the method 800 may generate a signal to operate the MR imaging component and receive and save as data in the memory 304,342 the signals generated by the MR imaging component during the operation of the MR imaging component.

At an optional block 818, the system may have a computed tomography (CT) imaging component that is electrically connected to the controller. When the body 202 is placed in the CT imaging component, the method 800 may generate a signal to operate the CT imaging component and receive and save as data in the memory 304,342 the signals generated by the CT imaging component during the operation of the CT imaging component.

At an optional block 820, the system may have a biopsy probe that is connectable to the positioning arm. The method 800 may generate a signal to move the positioning arm to position the biopsy probe in a position to perform an automated biopsy of an area of interest in the body and retrieve and store a biopsy sample taken by the biopsy probe.

At an optional block 822, the system may further have a needle that is connectable to the positioning arm. The method 800 may generate a signal to move the positioning arm to position the needle in a position to take a blood sample from the body 202 and retrieve and store the blood sample taken by the needle.

The blocks of the method 800 may be performed in any suitable order. For example, it may be desirable to take the blood sample at the block 822 before the body is exposed to any electromagnetic radiation at the blocks 814, 816, or 818.

Although the present disclosure provides examples in the context of performing an autopsy on a non-living body, example embodiments of the present disclosure may be used for performing other types of assessment of a body, including assessment on organs for the purpose of tissue harvesting and/or organ transplants. For example, the disclosed system and method may be used for performing an assessment of tissues and/or organs, shortly post mortem, to determine the quality and/or suitability of tissue(s) and/or organ(s). The information about the donor (e.g., age, sex, blood type, etc.) may be entered or linked into a centralized database or informatics system, with information about the condition of tissue(s)/organ(s) that are suitable for transplant. This information may be used to find matches or candidates in a database of patients awaiting transplants. This may enable a potential donor to be automatically matched with one or more patients for a potential tissue/organ transplant.

Having an automated system to perform this tissue/organ assessment may be less costly, quicker and/or more accurate than relying on a human surgeon, such probes and other tools may be mounted on the end effector of an automated robotic arm to perform real-time analysis. This may enable more effective assessment of the potential for tissue/organ donation within the optimum window post mortem and/or more effective identification of potential matches.

In one example, the medical navigation system 200 may have a guided path electrically coupled to the controller. The MR imaging component and/or the CT imaging component and/or the xray component may be in the form of an enclosure (e.g., the scanning module 700 shown in FIG. 7) enclosing at least a portion of the guided path. In one example, the scanning module 700 is located a distance from the positioning device, the guided path or a horizontal surface that is moveable on the guided path that supports the body, and the controller controls the guided path and/or the horizontal surface on the guided path to automatically position the body for access by the positioning device, the CT imaging component, the MR imaging component, and/or the x-ray imaging component when needed. The guided path may be a conveyor belt, tracks, rails and/or optical markers that may be followed by the positioning arm, or any other suitable solution that allows the medical navigation system 200 to move the body 202 for access by various components of an automated autopsy system.

While the teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

We claim:

1. A medical navigation system for performing at least part of an assessment of a non-living body, the medical navigation system comprising:
    a positioning device having a positioning arm with an end effector at an end of the positioning arm;
    an imaging device coupled to the end effector; and
    a controller electrically coupled to the positioning device and the imaging device, the controller having a processor coupled to a memory and a display; the controller being configured to:
    generate a signal to move the positioning arm to position the imaging device through a range of motion to perform a scan of a surface of the body;
    receive and save as data in the memory a signal generated by the imaging device during the range of motion; and
    perform a pathological analysis of the data in the memory that was saved data to automatically discover items of interest on the non-living body and provide an initial assessment of a likely cause of death;
    wherein in response to discovering an item of interest on the body, the processor is further configured to:
    generate a signal to automatically move the positioning arm to position the imaging device to capture additional images in an area of the item of interest on the body; and
    receive and save as additional data in the memory a signal generated by the imaging device during the capture of the additional images.

2. The medical navigation system according to claim 1 further comprising a substantially transparent horizontal surface upon which the non-living body rests allowing the imaging device to acquire images of a backside of the body.

3. The medical navigation system according to claim 1, wherein the imaging device is selected from a group consisting of an optical camera, a three dimensional (3D) camera, a video camera, a thermal camera, an acoustic receiver, a sonar device, an optical coherence tomography (OCT) device, and a polarization sensitive OCT (PS-OCT) device.

4. The medical navigation system according to claim 1, wherein the processor is further configured to assess suitability of at least one tissue or organ of the body for harvesting, based on the pathological analysis.

5. The medical navigation system according to claim 1, wherein the saved data is compared to other data stored in a database as a basis for the pathological analysis.

6. The medical navigation system according to claim 1, wherein the saved data is further stored in a repository as historical data for use in future assessments.

7. The medical navigation system according to claim 1, wherein the system further comprises a biopsy probe that is connectable to the end effector and the controller is further configured to:
  generate a signal to move the positioning arm to position the biopsy probe in a position to perform an automated biopsy of an area of interest in the body; and
  retrieve and store a biopsy sample taken by the biopsy probe.

8. The medical navigation system according to claim 1, wherein the system further comprises a needle that is connectable to the end effector and the controller is further configured to:
  generate a signal to move the positioning arm to position the needle in a position to take a blood sample from the body; and
  retrieve and store the blood sample taken by the needle.

* * * * *